United States Patent
Rebella et al.

(10) Patent No.: US 11,759,365 B2
(45) Date of Patent: Sep. 19, 2023

(54) DISPOSABLE SPECULUM WITH ADHESIVE SURFACE

(71) Applicant: Wisconsin Alumni Research Foundation, Madison, WI (US)

(72) Inventors: Gregory Rebella, Hartland, WI (US); James Berbee, Madison, WI (US); Azita Hamedani, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 683 days.

(21) Appl. No.: 16/744,739

(22) Filed: Jan. 16, 2020

(65) Prior Publication Data

US 2021/0220179 A1    Jul. 22, 2021

(51) Int. Cl.
| | |
|---|---|
| *A61F 11/00* | (2022.01) |
| *A61B 1/00* | (2006.01) |
| *A61B 1/227* | (2006.01) |
| *A61B 1/32* | (2006.01) |
| *A61B 17/00* | (2006.01) |

(52) U.S. Cl.
CPC ........ *A61F 11/006* (2013.01); *A61B 1/00103* (2013.01); *A61B 1/00105* (2013.01); *A61B 1/227* (2013.01); *A61B 1/32* (2013.01); *A61B 2017/00951* (2013.01)

(58) Field of Classification Search
CPC .. A61B 1/227; A61B 1/32; A61B 2017/00951
USPC .................................. 600/201–249, 201–245
See application file for complete search history.

(56) References Cited

U.S. PATENT DOCUMENTS

| | | | | |
|---|---|---|---|---|
| 4,785,796 | A | * | 11/1988 | Mattson ................. A61B 1/227 600/249 |
| 5,390,663 | A | | 2/1995 | Schaefer |
| 9,326,668 | B1 | * | 5/2016 | Berbee ............... A61B 1/00112 |
| 2002/0193665 | A1 | * | 12/2002 | Jones ................. A61B 1/00105 600/200 |
| 2005/0143626 | A1 | * | 6/2005 | Prescott ............ A61B 1/00087 600/162 |
| 2008/0208100 | A1 | | 8/2008 | Wolff |
| 2015/0279251 | A1 | * | 10/2015 | Matyear ................. H02S 40/30 362/249.02 |
| 2016/0067100 | A1 | * | 3/2016 | Cottier ................. A61F 11/006 606/162 |
| 2016/0374546 | A1 | | 12/2016 | Berbee et al. |

(Continued)

FOREIGN PATENT DOCUMENTS

| | | | |
|---|---|---|---|
| KR | 1020170117673 A | | 10/2017 |
| WO | 2014/186482 A1 | | 11/2014 |
| WO | 2019032689 A1 | | 2/2019 |

OTHER PUBLICATIONS

International Search Report for PCT/US2020/067197 filed on Dec. 28, 2020.

(Continued)

*Primary Examiner* — Eduardo C Robert
*Assistant Examiner* — Tara Rose E Carter
(74) *Attorney, Agent, or Firm* — Boyle Fredrickson S.C.

(57) ABSTRACT

A disposable speculum for an otoscope provides an attached forward-facing pressure sensitive adhesive for adhering to and extracting foreign bodies from the ear canal. Attaching the pressure sensitive adhesive to the speculum permits improved control, visualization, and reduced contamination of the pressure sensitive adhesive.

20 Claims, 9 Drawing Sheets

(56) References Cited

U.S. PATENT DOCUMENTS

| | | |
|---|---|---|
| 2018/0000336 A1 | 1/2018 | Gilad-Gilor et al. |
| 2018/0125345 A1* | 5/2018 | Rebella .............. A61B 1/00082 |
| 2019/0046359 A1* | 2/2019 | Hendricks .......... A61B 1/00135 |
| 2019/0209001 A1 | 7/2019 | Berbee et al. |

OTHER PUBLICATIONS

Nancy Van Keuls; The Lighted Ear Curette with Magnification; www.Bionix.com; 2016 Bionix Development Corp., Toledo, Ohio—(2) pages.

* cited by examiner

DISPOSABLE SPECULUM WITH ADHESIVE SURFACE

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to a speculum for an otoscope and in particular to a speculum providing an adhesive feature for removing foreign bodies from the ear canal.

Ear foreign body (foreign body) is a common complaint presenting to emergency departments, urgent care centers, and medical clinics. Such foreign bodies typically become lodged in the outer opening to the ear, the external auditory canal (EAC), which ends blindly at the tympanic membrane.

Due to its small size and highly sensitive skin, successful foreign body removal is often a challenge. As such, a variety of techniques have been described, however each has its limitations particularly when attempted in an ambulatory setting without access to sedation or other anxiolytic interventions. One technique is to utilize a small forceps to grasp the foreign body. While this may be successful for certain soft or organic materials, the most common foreign bodies are smooth surfaced which are not easily grasped with traditional forceps. Furthermore, directing light to provide adequate illumination to visualize the foreign body often requires assistance and frequent maneuvering from a second person. In the pediatric patient, a third person is typically required to assist in securing the child lest she move during the retrieval attempt, increasing the risk for unintentional injury or pushing the foreign body further into the canal. Additional devices, such as specialized hooks frequently employed by Ear Nose & Throat specialists also require patient cooperation or sedation and, due to the sharp nature of these tools, also present a risk for tympanic membrane or EAC injury. Other techniques such as use of suction and/or irrigation have limited success rates and can result in trauma to the tympanic membrane if the flushing is performed too aggressively.

In order to address these problems, it has been proposed to create a probe having a pressure-sensitive adhesive at one end which can be pressed against the foreign body to remove the foreign body as the probe is retracted. In one example, US patent publication US 20160067100 describes an angled probe having a pressure-sensitive adhesive on its tip.

The use of specialized probes of this type can be difficult in practice, requiring the healthcare professional to successfully maneuver the probe tip to the foreign body without contaminating the pressure-sensitive adhesive with earwax or the like, while attempting to view the foreign body (possibly with an otoscope displaced from the canal by the probe), obtain adequate illumination, and stabilize the patient against motion.

SUMMARY OF THE INVENTION

The present invention provides a pressure-sensitive adhesive supported by the tip of the speculum. The dimensions of the speculum naturally guide the pressure-sensitive adhesive away from contamination when the healthcare professional aligns the otoscope on the foreign body. The invention attaches the pressure-sensitive adhesive to the speculum in a way to preserve a view of the foreign body by the otoscope. When the speculum used with the otoscope can be of a size to reach the foreign body, the adhesive may be attached directly to the speculum rim. Alternatively, the pressure-sensitive adhesive may be displaced from the speculum rim by a short probe.

Specifically then, in one embodiment, the invention provides a speculum for an otoscope, the speculum having a sheath with a proximal sheath end adapted for retention on an otoscope and providing a central bore extending from the proximal sheath end to a bore rim at a distal sheath end along a sight-axis of the otoscope when the sheath is attached to the otoscope. The speculum further provides a pressure-sensitive adhesive supported by the sheath to extend forward from the sheath along the sight-axis to be guidable by the sheath into contact with a foreign body within an ear canal to attach to and retract the foreign body from the ear canal.

It is thus a feature of at least one embodiment of the invention to practically implement the benefits of a pressure-sensitive adhesive for foreign body removal by allowing continuous viewing of the foreign body through the speculum and stabilizing pressure-sensitive adhesive with the speculum structure and the natural use of the otoscope.

The sheath may provide an outer diameter and the pressure-sensitive adhesive provides a front facing surface positioned within the outer diameter from the sight-axis.

It is thus a feature of at least one embodiment of the invention to use the radial dimensions of the speculum to guide the pressure-sensitive adhesive away from the ear canal walls.

In this regard, the sheath may provide a funnel shape expanding an outer diameter of the sheath toward the proximal sheath end to progressively limit movement of the sheath perpendicular to the sight-axis as the sheath is inserted into the ear canal.

It is thus a feature of at least one embodiment of the invention to allow a useful bracing of the speculum against the ear canal for stabilization and better manipulation of the pressure-sensitive adhesive.

The speculum may include an elongate probe having a proximal probe end attached to the distal end of the sheath and sized to extend within the ear canal along the sight-axis to a distal probe end when the proximal sheath end is within the ear canal and the sensitive adhesive may be attached to a distal probe and extend forward therefrom.

It is thus a feature of at least one embodiment of the invention to independently position the pressure-sensitive adhesive within the field-of-view of the otoscope for viewing by the scope as well as allowing retaining the foreign body in the field-of-view.

The elongate probe may attach to a wall of the sheath and may be displaced from the sight-axis by a radius of a rim of the speculum and in a first portion, may extends therefrom displaced away from the sight-axis by at least the radius of the rim and then may curve toward the sight-axis at a second portion further beyond the sheath than the first portion.

It is thus a feature of at least one embodiment of the invention to provide a self-centering of the pressure-sensitive adhesive by contact between an inflexible probe and the ear canal wall so that the flexible probe may skate along the ear canal wall holding the pressure-sensitive adhesive away from that wall.

The elongate probe maybe be bent into a curve at its distal end to present a blunt front-facing surface as it is inserted into the ear canal.

It is thus a feature of at least one embodiment of the invention to provide a slender and, in some cases, flexible probe that presents a broad area forward surface providing greater adhesive area and reduced risk of tissue penetration.

The pressure-sensitive adhesive may be light transmissive, either translucent or transparent.

It is thus a feature of at least one embodiment of the invention to provide a pressure-sensitive adhesive that can permit through-imaging or through-light transmission for improved visualization of the foreign body The probe may provide a loop in a plane perpendicular to the sight-axis for supporting the pressure-sensitive adhesive.

It is thus a feature of at least one embodiment of the invention to provide a simple method of presenting a broad contact area in a slender probe.

The pressure-sensitive adhesive maybe distributed around the sight-axis allowing viewing of the foreign body along the sight-axis.

It is thus a feature of at least one embodiment of the invention to provide a broad area of a piece of contact that minimizes occlusion of the foreign body when viewed through the otoscope.

The pressure-sensitive adhesive may be displaced from the bore rim along the sight-axis by less than 10 millimeters.

It is thus a feature of at least one embodiment of the invention to retain the pressure-sensitive adhesive close to the speculum guided and protected by the speculum diameter.

The probe may provide a ductile material permitting manual adjustment of an angle of extent of the probe from the sheath when the probe is in a relaxed state.

It is thus a feature of at least one embodiment of the invention to permit manipulation of the probe by the healthcare professional to improve navigation through the ear canal or attachment to the foreign body.

The pressure-sensitive adhesive may provide a periphery around the sight-axis enclosing at least five square millimeters area provide a volume of at least 10 cubic millimeters.

It is thus a feature of at least one embodiment of the invention to make use of the close association between the speculum and the pressure-sensitive adhesive to maximize the contact area of the pressure-sensitive adhesive while preserving field-of-view of the foreign body.

In one embodiment, the pressure-sensitive adhesive may be attached in contact with the bore rim of the speculum.

It is thus a feature of at least one embodiment of the invention to minimize obstruction of the field-of-view of the otoscope while providing a large contact area between the pressure-sensitive adhesive and the foreign body.

The invention may be used with a camera-based otoscope having a handgrip for support by a healthcare professional and a camera stalk extending from the handgrip to a distal end receivable within an ear canal. A camera may be at the distal end of the ear canal to provide a field-of-view therefrom. In this case, the pressure-sensitive adhesive maybe sized to occupy no more than half of the field-of-view when centered in the field-of-view.

It is thus a feature of at least one embodiment of the invention to tailor pressure-sensitive adhesive into the field-of-view of the otoscope to provide a flexible trade-off between adhesive size and visibility.

In one embodiment, the pressure-sensitive adhesive may be integrated into a source of illumination providing a light pipe serving in a manner analogous to the speculum to help guide the adhesive away from the auditory canal.

These particular objects and advantages may apply to only some embodiments falling within the claims and thus do not define the scope of the invention.

DETAILED DESCRIPTION OF THE PREFERRED EMBODIMENT

I. Speculum

Figure 1:
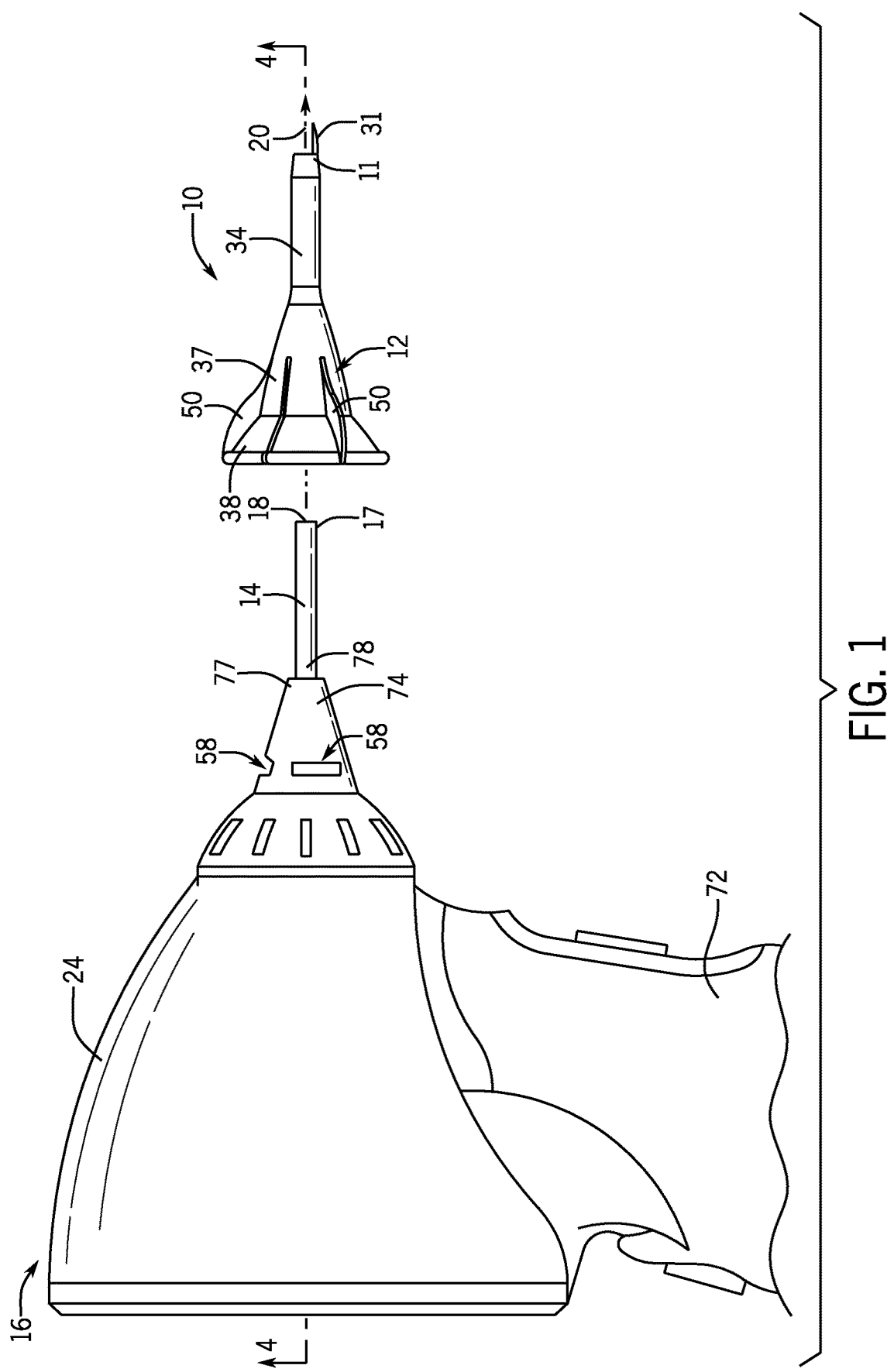
FIG. 1 is a side elevation view of a disposable speculum constructed according to one embodiment of the present invention being inserted onto an otoscope along an insertion axis.

Referring initially to FIG. 1, a removable speculum 10 of the present invention may provide a protective sheath 12 that fits over a cylindrical probe 14 of an otoscope 16 extending along an insertion sight-axis 20 that aligns with the ear canal when the otoscope 16 is used. The otoscope 16 may support on its distal probe tip 17 a front facing electronic camera 18 for acquiring multi-pixel, three-color images in a field-of-view directed along a sight-axis 20. An otoscope 16 suitable for use with the present invention is described in U.S. Pat. No. 9,326,668, US patent publication 2016/0374546, and US patent publication 2018/0125345, each of which is hereby incorporated by reference.

The removable speculum 10 is attached to the otoscope 16 by a snap lock engagement between the protective sheath 12 and the otoscope 16 supporting the cylindrical probe 14 and electronic camera 18 as further described below.

Figure 2:
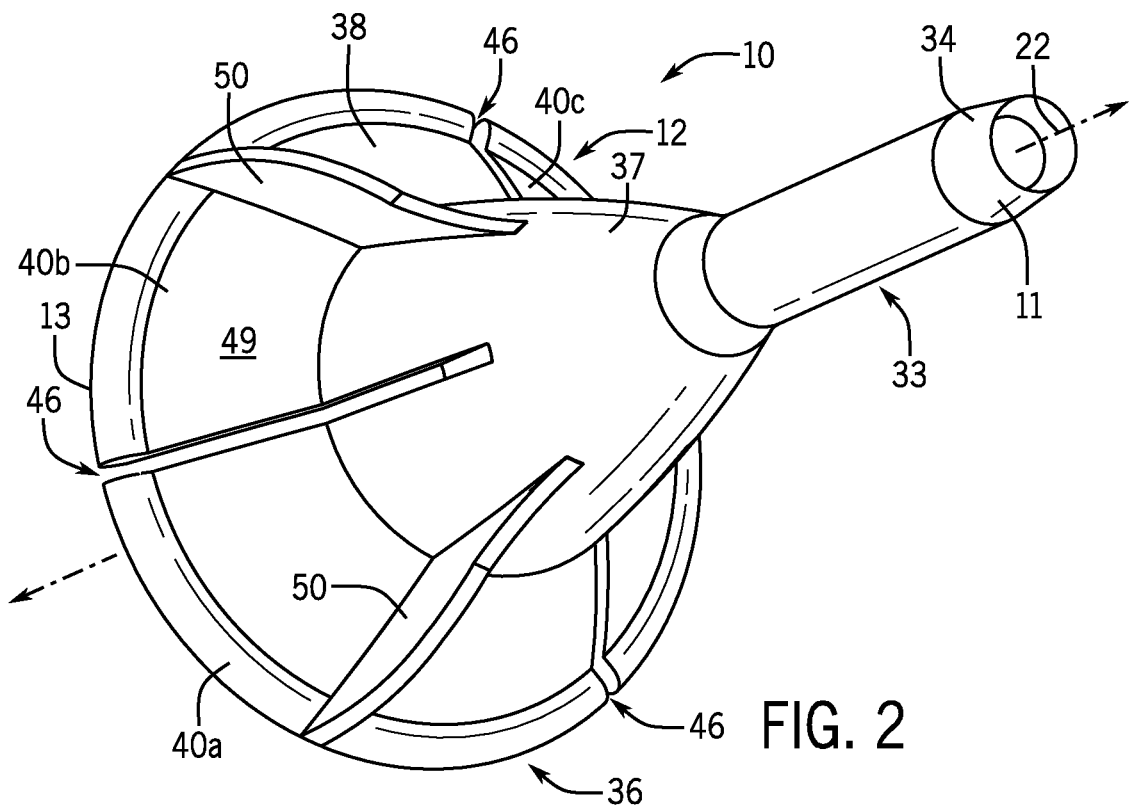
FIG. 2 is a perspective view of an exterior of the disposable speculum of FIG. 1 providing a sheath presenting a flexing collar tapering to a cylindrical tube.

Referring now to FIG. 2, the protective sheath 12 of the removable speculum 10 may be in the form of a hollow trumpet with a central bore extending along the sight-axis 20 and surrounded by the outer sheath 12. The outer sheath 12 is generally radially symmetric at 120 degrees of rotation with progressively increasing amounts of outward flaring along the sight-axis 20 as the sheath 12 flares upward from a distal sheath end 11 to a circular, outer proximal rim 13 attached to the otoscope 16. An outer diameter of the outer sheath 12 may progressively increase from approximately 2-3 mm of the distal sheath end 11 to approximately 18-19 mm of the outer proximal rim 13, or progressively increase by 6 to 10 times its minimum diameter.

The outer sheath 12 may be constructed of a non-elastomeric thermoplastic by injection molding. The rigid material of the protective sheath 12 allows the speculum 10 to easily slide over the cylindrical probe 14 without the resistance that might be expected, for example, if the material were an elastomer. The rigid material of the protective sheath 12 also serves to support and protect the relatively fragile cylindrical probe 14 and electronic camera 18. The speculum 10 may be opaque and may be light absorbing, such as black in color, to minimize light leakage into the sheath 12.

A distal portion 33 of the protective sheath 12 extending into the ear canal may provide an elongate tube 34 having a central bore extending along the sight-axis 20, with an inner diameter, measured in a plane perpendicular to sight-axis 20, of slightly less by the thickness of the protective sheath 12 then approximately 2-3 mm and less than 3 mm and desirably less than 2.3 mm. It is intended that the tube 34 be sized with an outer diameter that is smaller than the ear canal so that it may be inserted therein comfortably, for example, approximately 2-3 mm and less than 3 mm and desirably less than 2.4 mm. The outer diameter of the tube 34 may be minimized to allow for insertion of the tube 34 into smaller sized ear canals, for example, those of toddlers and infants which may be as small as 3 to 4 mm in diameter. A length of the tube 34 may be approximately 8-12 mm and at least 8 mm to allow the protective sheath 12 to extend past minor obstructions, such as normally present earwax, but allow passage of the held electronic camera 18 proximate to the ear drum to allow for imaging of the ear drum of the ear.

In certain embodiments, the tube 34 may be cylindrical with a constant inner diameter closely matching the outer diameter of the cylindrical probe 14 for good support, although the tube 34 may also be slightly tapered over this length, for example, tapering toward the narrowed distal sheath end 11.

The tube 34 is open at the distal sheath end 11 to allow the held electronic camera 18 to be exposed along the sight-axis 20. The distal sheath end 11 may support a probe or a tool, for example, a scoop 31, assisting with the removal of ear wax. The scoop 31 extends from the distal sheath end 11 along the axis 22 and is upwardly concave toward the axis 22.

A proximal portion 36 of the protective sheath 12 may take the form of a funnel 37 having a central bore flaring outwardly from the tube 34 and extending to an increasingly flaring, integrally molded collar 38 coupling with the otoscope 16. A diameter of a distal end of the funnel 37, measured in a plane perpendicular to the sight-axis 20, may be approximately 2-3 mm, and a diameter of a proximal end of the funnel 37, extending from the distal end of the funnel 37 along the sight-axis 20 by at least 12 mm, may be 9-10 mm. The funnel 37 may be flared outwardly toward the integrally molded collar 38 of the protective sheath 12 at approximately 15-20 degrees from the sight-axis 20 and approximately 18 degrees from the sight-axis 20. The increased diameter of the funnel 37 compared to the narrow tube 34 may assist in controlling the insertion depth of the speculum 10 such that the proximal portion 36 can only extend partially into the ear canal 21 to prevent the distal tube 34 from extending too deeply into the ear canal 21 which would risk damaging or puncturing the ear drum.

The funnel 37 expands outwardly to the increasingly flaring, integrally molded collar 38 which is engageable over a head portion 24 of the otoscope 16 to be secured thereon. The collar 38 may take a similar conical shape, flaring outwardly toward the proximal end of the protective sheath 12 at approximately 40-45 degrees from the sight-axis 20 and approximately 45 degrees from the sight-axis 20, in a non-flexed state, providing a greater diameter bore for receiving the head portion 24 of the otoscope 16. A diameter of a distal end of the collar 38, measured in a plane perpendicular to the sight-axis 20, may be approximately 9-10 mm, and a diameter of a proximal end of the collar 38, extending from the distal end of the collar 38 along the sight-axis 20 by at least 3 mm, may be 18-19 mm.

The proximal portion 36 of the protective sheath 12 may provide flexing segments 40 formed by axial slots 46 extending along sight-axis 20 and separating the proximal portion 36 into cantilevered sections that are flexible outwardly and/or inwardly by a distance of approximately 0.1-0.5 mm, and at least 0.1 mm, away from and/or toward the sight-axis 20 at its proximal rim 13. The longitudinally extending slots 46 may be approximately 0.5-1 mm wide and at least 0.5 mm wide and may extend through the proximal rim 13 toward the distal tube 34 at length of at least 8 mm, or at least one-third the length of the protective sheath 12.

In one embodiment the collar 38 may include three equally spaced slots 46 positioned approximately 120 degrees apart about the sight-axis 20 of the proximal portion 36 and forming three cantilevered segments 40a, 40b, 40c supported at a distal end by the protective sheath 12 and detached on left and right sides by the slots 46 and at the proximal rim 13 to allow for outward and/or inward flexure of the segments 40a, 40b, 40c away from and/or toward the sight-axis 20. Each of the segments 40a, 40b, 40c may be independently flexed; however, equal outward/inward forces on segments 40a, 40b, 40c will generally result in substantially equal outward/inward flexure of each segment 40a, 40b, 40c.

An exterior surface 49 of the proximal portion 36 of the protective sheath 12 may support at least one outwardly protruding fin 50 extending from the protective sheath 12. The at least one outwardly protruding fin 50 may generally span between the funnel 37 and the collar 38 to form a generally triangular tab for finger twisting of the protective sheath 12 by a healthcare professional without the need for additional tools. In one embodiment, the proximal portion 36 may carry three equally spaced fins 50 spaced approximately 120 degrees apart about the sight-axis 20 and generally radially centered between the three equally spaced slots 46 described above.

Figure 3:
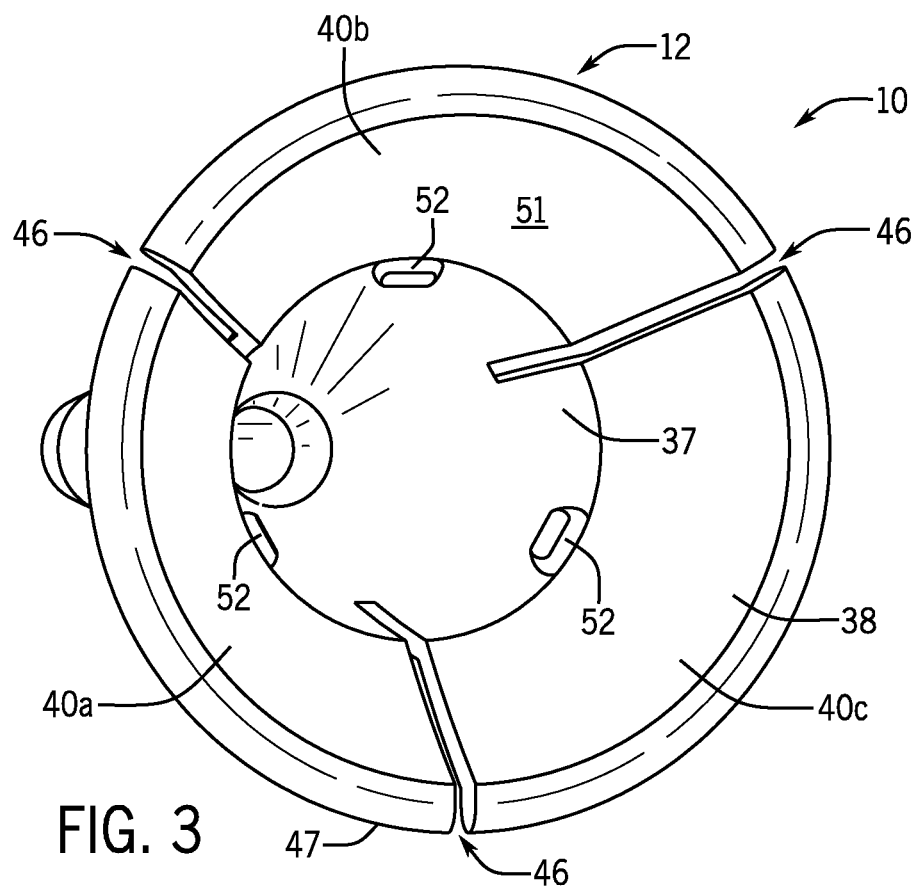
FIG. 3 is a perspective view of an interior of the disposable speculum of FIG. 2 showing multiple teeth flexing outwardly with the flexing collar.

Referring to FIG. 3, an interior surface 51 of the proximal portion 36 may support at least one radially inwardly projecting tooth 52 engaging the inserted head portion 24 of the fully installed otoscope 16. The tooth 52 may take the shape of an oval, oblong, or rectangular projection extending from the interior surface 51 toward the sight-axis 20 and having generally rounded outer edges allowing for a sliding or rolling transition of the tooth 52 into and out of a corresponding groove 58 of the otoscope 16. The tooth 52 may be at least 1 mm in width, 3 mm in length, and 0.1 mm in depth. The tooth 52 may be oriented so that a longest dimension of the tooth 52 extends along a circumference of the protective sheath 12 while the shortest dimension of the tooth 52 extends along the sight-axis 20.

Figure 5:
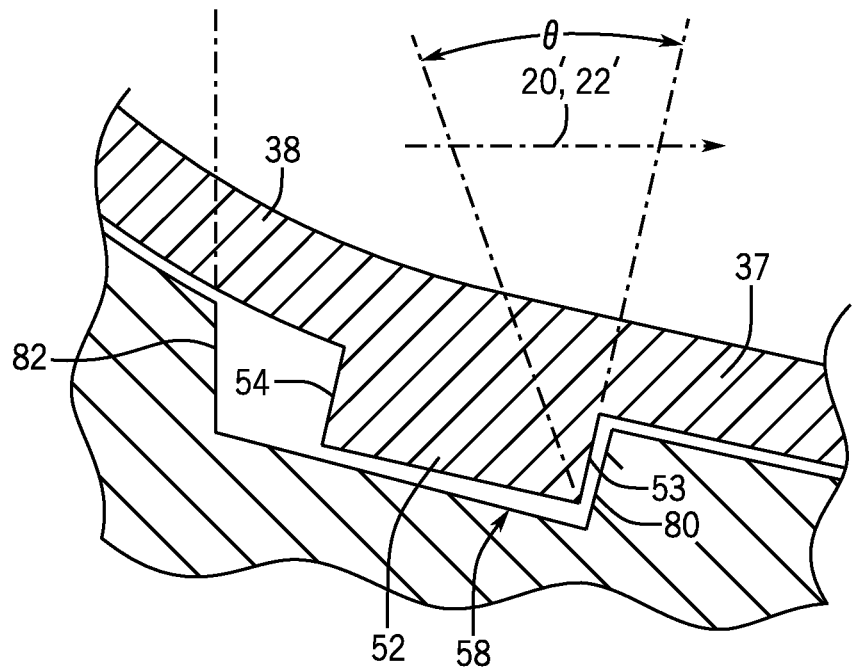
FIG. 5 is an enlarged cross-sectional view similar to FIG. 4 showing a tooth received into a groove of the otoscope having substantially perpendicular sidewalls.
Figure 6:
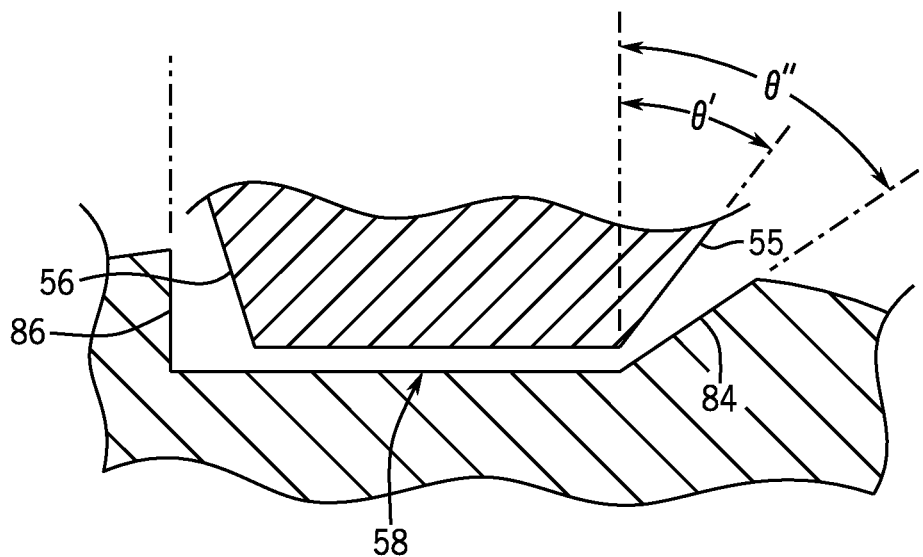
FIG. 6 is an enlarged cross-sectional view, along a vertical plane along lines 6-6 of FIG. 4, perpendicular to the insertion axis of the otoscope showing the tooth received into the groove of the otoscope having at least one ramped sidewall.

Turning briefly to FIGS. 5 and 6, each tooth 52 may have a front face 53 facing toward a distal end of the protective sheath 12 that is substantially perpendicular to the sight-axis 20 (axis 22' running parallel to axis 22), as shown, or may also be canted toward the sight-axis 20 as one moves inwardly along the front face 53, and thus oriented to abut the front wall of the groove 58 to prevent removal of the tooth 52 from the groove 58 in a forward direction. A rear face 54 of the tooth 52 may be substantially perpendicular to the sight-axis 20, as shown, or may be canted toward the sight-axis 20 as one moves outwardly along the front face 53, and thus oriented to abut the rear wall of the groove 58 to prevent removal of the tooth 52 from the groove 58 in a rearward direction. Side faces 55, 56 of the tooth 52 may be canted away from the sight-axis 20 as one moves inwardly along the front face 53, as shown, but may also be canted toward the sight-axis 20 as one moves inwardly along the front face 53, or may be substantially perpendicular to the sight-axis 20, and thus oriented to assist with moving the tooth 52 up a ramp of the groove 58. In one embodiment, an interior surface 51 of each segment 40a, 40b, 40c may support a single tooth 52. The teeth 52 may be generally centered within each segment 40a, 40b, 40c, between the three equally spaced slots 46, and positioned toward the proximal end of funnel 37. The teeth 52 may be rotationally aligned with the outwardly extending fins 50.

Figure 4:
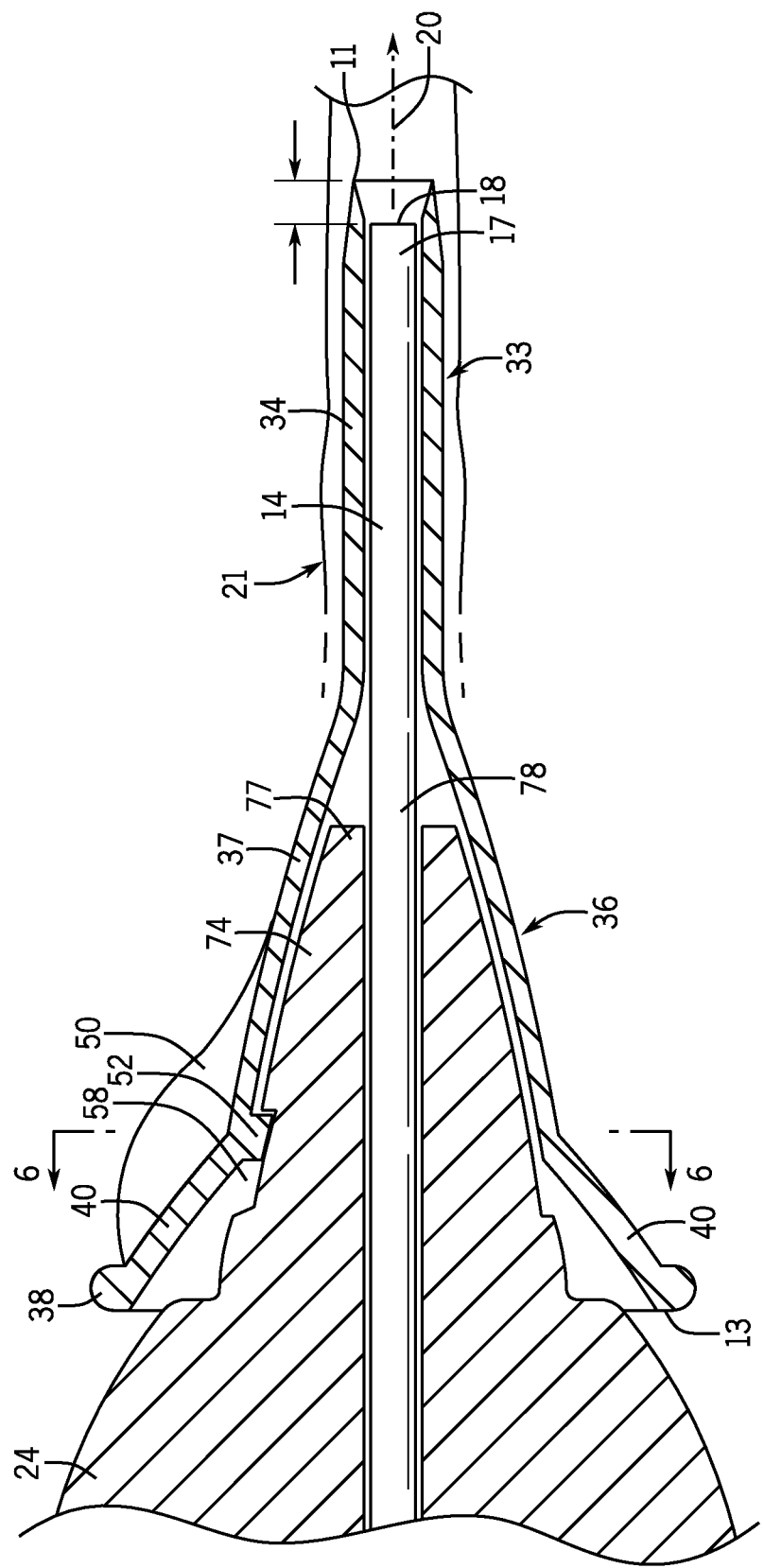
FIG. 4 is a cross-sectional view, along a vertical plane along lines 4-4 of FIG. 1 through the speculum and assembled otoscope of FIG. 1.

Referring now to FIGS. 1 and 4, the removable speculum 10 may slide over an otoscope 16 generally providing a housing having a head portion 24 held up by a detachable grip portion 72. The grip portion 72 is sized to be grasped by the hand of a healthcare professional in the manner of a conventional otoscope with the grip portion 72 extending generally upward from the healthcare professional's hand to the head portion 24.

The head portion 24 of the otoscope 16 may take the shape of a circular cone tapering to a front end defined by a circular tip supporting a frustoconical mounting boss 74. A distal end 77 of the frustoconical mounting boss 74 of the head portion 24 of the otoscope 16 supports the extension of the cylindrical probe 14 having a proximal end 78 supported by the head portion 24 and distal end or tip 17 that extends along the sight-axis 20 of the ear canal 21. The cylindrical probe 14 may extend approximately a length of 8-10 mm and at least 8 mm, to allow the front facing electronic camera 18 at the distal probe tip 17 to reach a desired depth within the ear canal 21. The distal tip 17 of the cylindrical probe 14 supports the electronic camera 18 for viewing into the ear canal 21 and communicating with an electronic display displaying the otoscope image from the electronic camera 18 and is positioned at the distal tip 17 of the cylindrical probe 14 along the sight-axis 20 and centered along the sight-axis 20 as understood in the art. The electronic camera 18 may, for example, be a self-contained charge coupled device (CCD) camera such as is commercially available providing, for example, a measurement area of 1.4 mm diagonal and 62,500 pixels.

An outer rim of the frustoconical mounting boss 74 may provide grooves 58 therein and corresponding with the teeth 52 of the removable speculum 10. The grooves 58 of the otoscope 16 may be generally rectangular holes approximately 1 to 2 mm in width, 3 to 4 mm in length, and 0.1 to 0.5 mm in depth. In one embodiment, the cylindrical mounting boss 74 may support three equally spaced grooves 58 spaced approximately 120 degrees apart about sight-axis 20 whereby a greatest dimension of the rectangle extends along a circumference of the cylindrical mounting boss 74 and a shortest dimension of the rectangle extends along sight-axis 20.

Referring now to FIG. 5, the rectangular grooves 58 may provide front and rear substantially perpendicular sidewalls 80, 82 (to sight-axis 20' parallel to sight-axis 20), respectively, preventing the teeth 52 from being removed from the grooves 58 in forward and rear directions along the sight-axis 20. In this manner, the removable speculum 10 cannot be easily removed by the healthcare professional and is secured to the otoscope 16 once installed.

Referring now to FIG. 6, the rectangular grooves 58 may provide lateral sidewalls 84, 86 whereby at least one of the sidewalls 84, 86 is angled to provide a ramp in which the tooth 52 may slide or ride up the angled sidewall 84, 86 and become disengaged from the groove 58 when the removable speculum 10 is rotated in at least one of a clockwise or counterclockwise direction. The angulation of at least one of the sidewalls 84, 86 may be at least 45 degrees from perpendicular and at least 45 degrees. It is understood that one or both of the lateral sidewalls 84, 86 may be angled to provide an exit ramp for the tooth 52. In one embodiment, one lateral sidewall 84 is angled while the opposite sidewall 86 extends substantially perpendicular to the floor of the groove 58. In this respect, twisting motion in one direction (toward the angled sidewall 84) will allow for the removal of the removable speculum 10 from the head portion 24 of the otoscope 16 while twisting motion in the opposite direction will be prevented by the substantially perpendicular sidewall 86. In an alternative embodiment, both lateral sidewalls 84, 86 are angled such that twisting in either clockwise or counterclockwise directions will allow for the removal of the removable speculum 10 from the head portion 24 of the otoscope 16.

Referring again to FIGS. 1, 4 and 5, the removable speculum 10 may be inserted over the cylindrical probe 14 by sliding the speculum 10 rearward along the insertion sight-axis 20 over the cylindrical probe 14 whereby the central bore of the tube 34 holds the cylindrical probe 14 carrying the front facing electronic camera 18 at its tip 17. The segments 40*a*, 40*b*, 40*c* of the removable speculum 10 may flex outward to accommodate the head portion 24 as it is inserted into the speculum 10. The speculum 10 is inserted along sight-axis 20 until the collar 38 extends over the boss 74 of the removable speculum 10. The speculum 10 may not need to be rotated if the teeth 52 are aligned with the grooves 58 when inserted along sight-axis 20 but in some cases may need to be slightly rotated (less than a quarter turn) until the teeth 52 align with the grooves 58 and the removable speculum 10 snaps into place.

Once installed, the axial position of the distal sheath end 11 of the removable speculum 10 is set so that the distal tip 17 of the cylindrical probe 14 may terminate before the distal sheath end 11 of the removable speculum 10. In one embodiment, the distance between the distal tip 17 of the cylindrical probe 14 and the distal sheath end 11 of the removable speculum 10 may be approximately 1-2 mm, or less than 2 mm. The distance between the distal tip 17 of the cylindrical probe 14 and the distal sheath end 11 of the removable speculum 10 may be set to minimize blinding internal reflection and narrowed field-of-view of the electronic camera 18 while still protecting the fragile electronic camera 18 from contamination and damage.

Referring again to FIG. 6, an approximately quarter turn twist of the removable speculum 10 slides the tooth 52 along one of the angled sidewalls 84, 86 while the segments 40*a*, 40*b*, 40*c* of the removable speculum 10 flex outward (at least 0.1 mm) to accommodate the outward movement of the tooth 52. Once the tooth 52 is displaced from the groove 58, forward motion of the removable speculum 10 along the sight-axis 20 allows the removable speculum 10 to be detached from the head portion 24 of the otoscope 16.

As is generally understood, the outer ear of a human patient includes a pinna providing a sound collecting structure. The pinna surrounds the ear canal 21 leading to and terminating at the tympanic membrane or eardrum. A length of the ear canal 21 in an average adult human is approximately 25 mm and the ear canal 21 has an average diameter of approximately 7 mm. A length of the ear canal 21 in an average infant is approximately 5 mm and the ear canal 21 has an average diameter of approximately 3-4 mm.

II. Foreign Body Removal Tool

Figure 7:
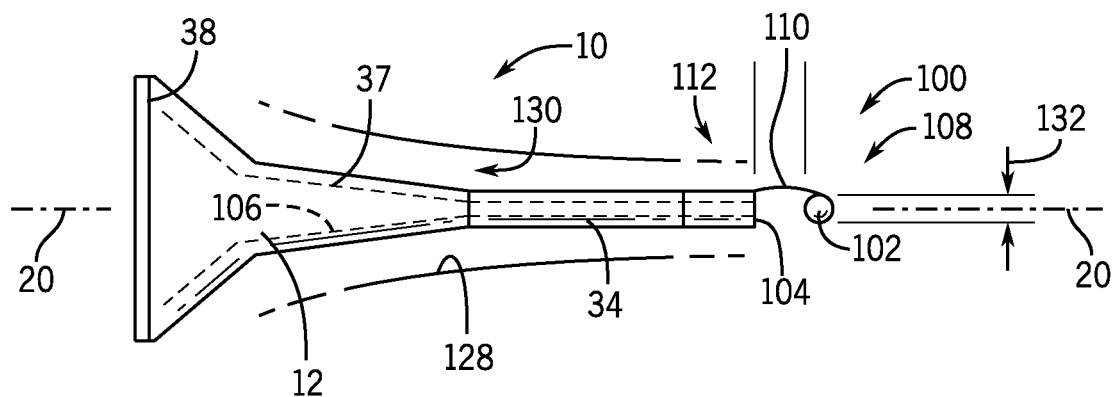
FIG. 7 is a side elevational view of an alternative embodiment of the speculum of FIG. 1 providing a pressure-sensitive adhesive element for removal of foreign bodies from a human ear.

Referring now to FIG. 7, the speculum 10 may provide a foreign body removal tool 100 using a pressure-sensitive adhesive 102. In one embodiment, the pressure-sensitive adhesive 102 maybe positioned along the sight-axis 20 of the speculum 10 forward from a rim 104 of an internal bore 106 of the sheath 12 and generally coaxial about the sight-axis 20.

Figure 8:
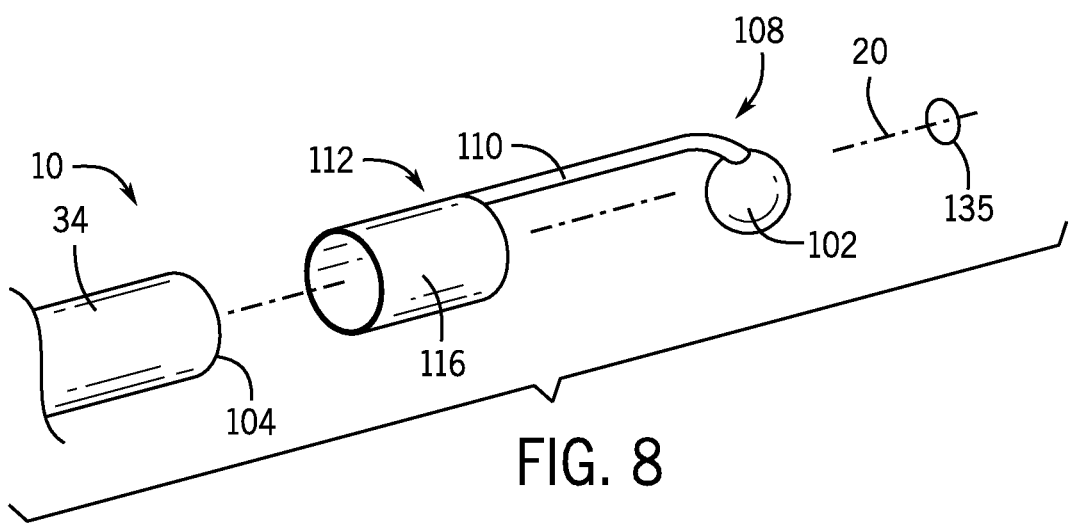
FIG. 8 is a perspective, exploded fragmentary view of an end of the speculum of FIG. 7 showing attachment of a support probe for holding the pressure-sensitive adhesive positioned in alignment with the sight-axis of the speculum.

Referring also to FIG. 8, in one embodiment, the pressure-sensitive adhesive 102 is supported on a distal end 108 of a probe wire 110 whose proximal end 112 is attached to an outer wall of the sheath tube 34 at the bore rim 104. In this embodiment, the probe wire 110 spaces the pressure-sensitive adhesive 102 by a distance of 3 to 4 millimeters along the sight-axis 20 in front of the bore rim 104 and roughly centers the pressure-sensitive adhesive 102 on the sight-axis 20. The proximal end 112 of the probe wire 110 may be attached, for example, to the outer wall of the sheath tube 34 by a thin tape 116, a molded sleeve, adhesive, or other techniques generally known in the art.

The probe wire 110 in one embodiment may be a ductile or malleable wire allowing manual bending of the probe wire 110 to permanently change an angle of extension of the probe wire 110 from the speculum 10 with respect to the sight-axis 20. In this way, the position of the pressure-sensitive adhesive 102 may be adjusted with respect to that sight-axis 20. A soft iron wire coated with a polymer may be suitable for the probe wire 110 having a gauge of 30 to 40 and possibly including a spiral wound pair of such wires for additional stiffness.

In one example, the pressure-sensitive adhesive 102 may be a spheroidal bead having a diameter of 2 to 4 millimeters and/or a volume of greater than 10 cubic millimeters. The shape of the pressure-sensitive adhesive 102 may be such as to provide a forwardly exposed area of at least five square millimeters.

Suitable pressure-sensitive adhesive materials for the pressure-sensitive adhesive 102 include a one-part, high-tack, hot-melt adhesive having an optically clear or translucent quality and providing a suitable viscosity when cooled to prevent free-flowing under its own weight, for example, a viscosity exceeding 100,000 centipoise and typically as high as 500,000 centipoise. As is generally understood in the art, pressure-sensitive adhesives are adhesives that do not require a chemical reaction and which form a bond when pressure is applied. No solvent, water, or heat is needed to activate the adhesive. In a one embodiment, the adhesive has a tack strength of greater than 350 and ideally greater than 800 and less than 1550 grams measured by Polyken Tack Testing on a 1" square per ASTM D2979-01 using a 5.0 mm probe, 2 mil polyester carrier. See F. H. Hammond, "Polyken Probe Tack Tester;" In STP360-EB Adhesion, (pp. 123-134). West Conshohocken, Pa.: ASTM International, 1964. STP44569S. The peel strength in pounds per inch may be between 1 and 10 using 90° Peel Testing on 1"×3-10" strip. QPC 3060, Ref ASTM D3330: 24 hour dwell, stainless steel.

Figure 9:
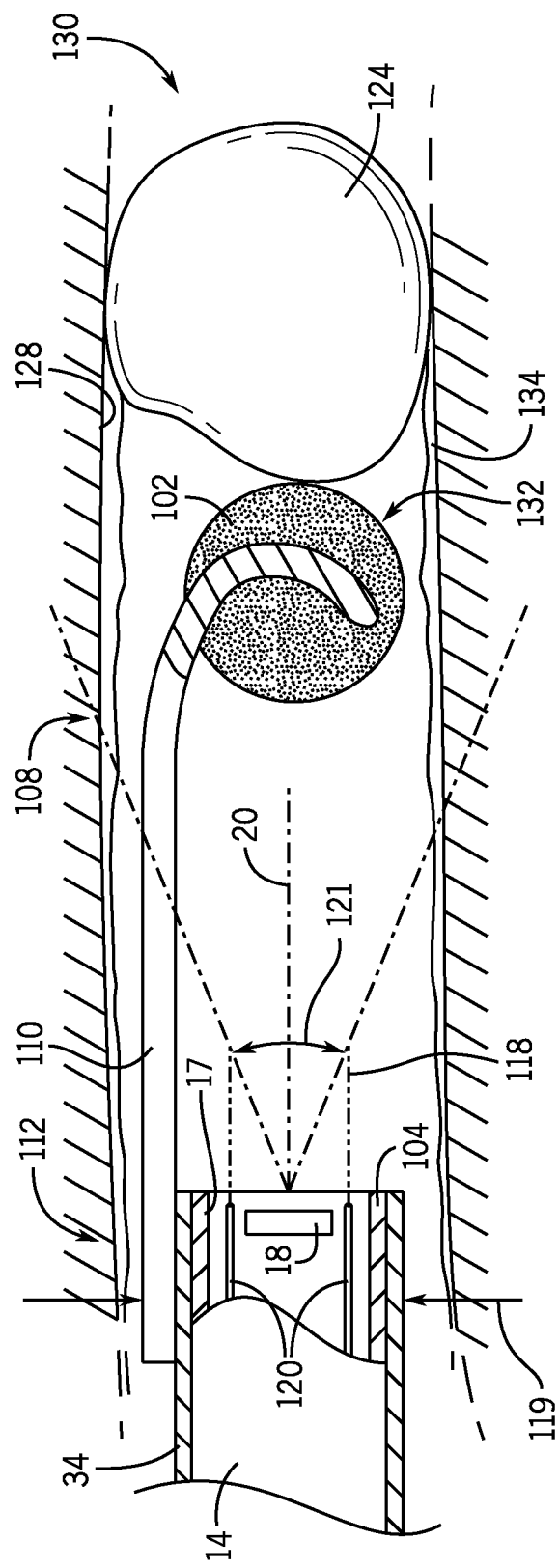
FIG. 9 is a fragmentary, elevational cross-section of the speculum of FIGS. 7 and 8 positioned within an ear canal for extraction of a foreign body showing the field-of-view of the camera of the otoscope and a skating action possible with the support wire to center the pressure-sensitive adhesive in the ear canal.

Referring now to FIG. 9, in one embodiment, the probe wire 110 may pass generally parallel to the sight-axis 20 from its point of attachment to the outer wall of the tube 34. The probe wire 110 will be displaced to a side of the sight-axis 20, for example, by the radius of the tube 34, and will be offset from the illumination axes 118 of light emitting optical fibers 120 flanking the camera 18 and offset from a center of illumination rays from each optical fiber 120 generally parallel to the sight-axis 20. Generally, the sight-axis 20 will centered within the angle-measured field-of-view 121 of the camera 18 and some of the probe wire 110 will be outside of the field-of-view 121. At a distal end of the probe wire 110, the probe wire 110 may curve inward toward the sight-axis 20 to position the pressure-sensitive adhesive 102 into the field-of-view 121 generally centered along the sight-axis 20 to receive illumination along the illumination axes 118. Generally, the pressure-sensitive adhesive 102 will be positioned within the outer periphery or diameter 119 of the speculum 34 as it is extended along the axis 20 to allow stabilization of the pressure sensitive adhesive 102 by skating or bracing the surface of that diameter 119 along the inner surfaces of the ear canal. The diameter 119 will generally be measured perpendicularly to axis 20.

Figure 10:
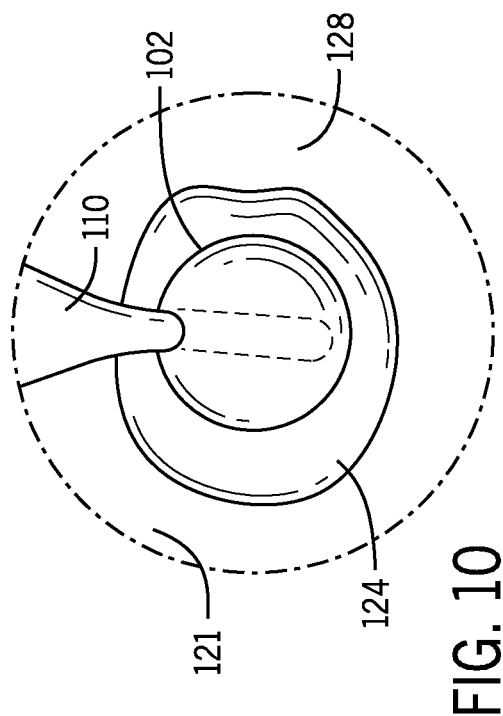
FIG. 10 is an image from the camera of FIG. 9 showing the relative field-of-view of the otoscope and size of the pressure-sensitive adhesive therein.

Referring also to FIG. 10, as so positioned, the pressure-sensitive adhesive 102 occupies only a portion of the field-of-view 121 of the camera 18, for example, less than 50 percent of the area, and desirably less than 30 percent of the area, allowing visualization of a foreign body 124 from behind the pressure-sensitive adhesive 102. In this regard, the pressure-sensitive adhesive 102 is desirably translucent or transparent (light transmitting) to allow either the illumination of the foreign body 124 through the pressure-sensitive adhesive 102 and/or partial visualization of the foreign body 124 through the pressure-sensitive adhesive 102, or visualization of an area of contact with the foreign body 124 and the pressure-sensitive adhesive 102 caused by changes in reflection when the two bodies touch.

Referring again to FIG. 9, the outboard extent of the probe wire 110 and its flexible nature allow the probe wire 110 to attach to the outer surface of the sheath tube 34 displaced by the radius of the sheath tube from the axis 20 to ride along an inner wall 128 of the ear canal 130 for most of its length until curving back toward the axis 20 at its distal end. This form serves to hold the pressure-sensitive adhesive 102 and its front contacting surface 132 away from earwax 134 and oils lining the ear canal 130 thus preserving the tacky nature of the pressure-sensitive adhesive against contamination and degradation. For this purpose, the probe wire 110 may be bowed outward slightly to provide a slight spring biasing against the ear canal 130 in the surface that can ride along the inside of the ear canal 130.

The distal end 108 of the probe wire 110 may curve backward toward the camera 18 so as to provide a blunt surface and broader contact area between the foreign body 124 and pressure-sensitive adhesive 102 providing greater adhesion and limiting forces that would urge the foreign body 124 deeper into the ear canal 130.

The ability to use a relatively large bead of (e.g., three millimeters diameter) pressure-sensitive adhesive 102 is practical because of a relatively large field-of-view 121 possible when the camera 18 is positioned near the end of the probe 14.

Figure 11:
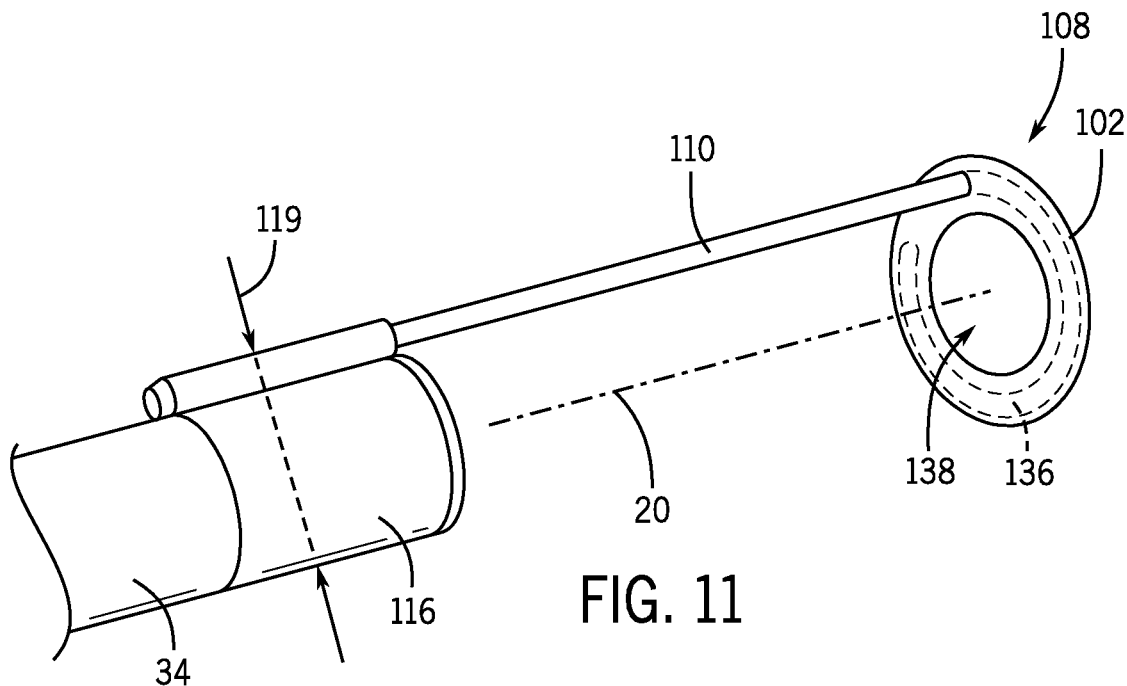
FIG. 11 is a figure similar to that of FIG. 8 showing an alternative embodiment where the pressure-sensitive adhesive has a doughnut form and is supported on a loop running around a central aperture centered on the sight-axis of the otoscope.
Figure 12:
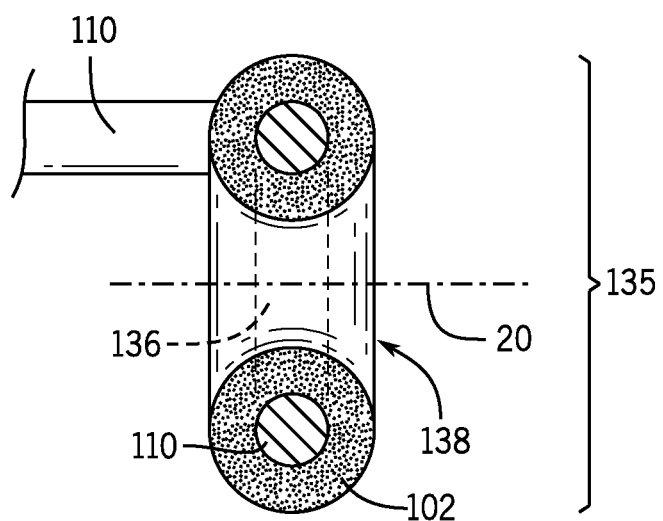
FIG. 12 is an elevational, side, cross-sectional view of the embodiment of FIG. 8 showing the orientation of the loop with respect to the sight-axis.

Referring now to FIGS. 11 and 12, in an alternative embodiment, the distal end 108 of the probe wire 110 may be formed in a loop 136, generally passing in a plane perpendicular to the sight-axis 20 and coated with pressure-sensitive adhesive 102 in a doughnut configuration providing a central opening 138 aligned with the sight-axis 20. The central opening 138 allows improved visualization of the foreign body 124 (shown in FIG. 9) through the central opening 138 while still providing a large contact area on a front surface 132 of the pressure-sensitive adhesive 102, for example, providing a frontal area of contact of greater than five cubic millimeters. The loop 136 further creates a blunt forward-facing surface reducing the risk of puncture or injury to the ear. Desirably the central opening 138 allows unobstructed transmission of light from the optical fibers 120 of FIG. 9; however, a translucent or transparent pressure-sensitive adhesive 102 may allow some blockage of the optical fibers 120 while still providing good illumination. In some embodiments, the pressure-sensitive adhesive 102 acts as a diffuser of light, this diffuse light providing a visual clue of proximity between the pressure-sensitive adhesive 102 and the foreign body 124 when the foreign body 124 becomes noticeably brighter only in close proximity to the loop 136.

Figure 13:
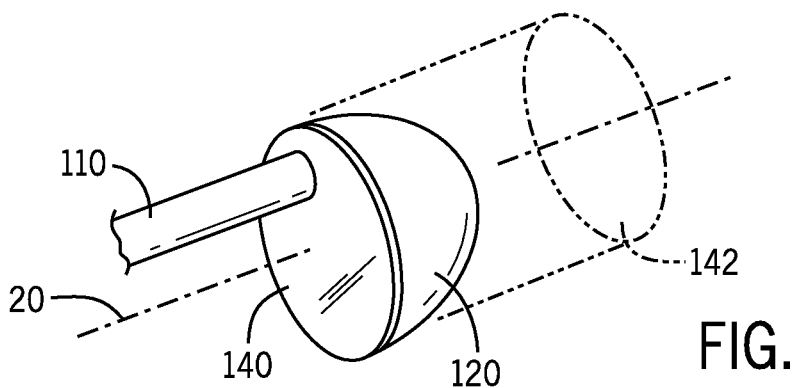
FIG. 13 is a figure similar to that of FIG. 11 showing solid panel replacing the loop which may be transparent to provide a view therethrough.

Referring now to FIG. 13 it will be appreciated that the loop 136 of FIGS. 11 and 12 may be replaced with a disk 140 also passing in a plane perpendicular to the sight-axis 20, for example, of a transparent material having a broad face for supporting the pressure-sensitive adhesive 102 to provide improved visualization through the pressure-sensitive adhesive 102. The disk 140 provides a broad area 142 of exposed front surface of the pressure-sensitive adhesive 102, as is desired for good contact and attachment forces by the pressure-sensitive adhesive 102 to the foreign body (shown in FIG. 9), without the need for a central opening that limits contact area.

The previously described embodiments may provide location of the pressure-sensitive adhesive 102 at or near the focal point of the camera 18 for good visualization thereof and of the foreign body 124 when the two are connected and to minimize blockage of the field-of-view 121. In an alternative embodiment, shown in FIG. 14, the pressure-sensitive adhesive 102 may be placed, for example, in small dots 144 directly on the circular bore rim 104 of the tube 34 at its distal end. Alternatively, as shown in FIG. 15, the pressure-sensitive adhesive 102 may be formed in a doughnut form 146 conforming to the diameter of the bore rim 104 and attached thereto. In both of these cases the pressure-sensitive adhesive 102 may be entirely outside of the field-of-view 121 of the camera 18 but nevertheless protected from contamination by material on the inner walls 128 of the ear canal 130 by the outer surface of the tube 34 which itself may ride against those walls.

Figure 14:
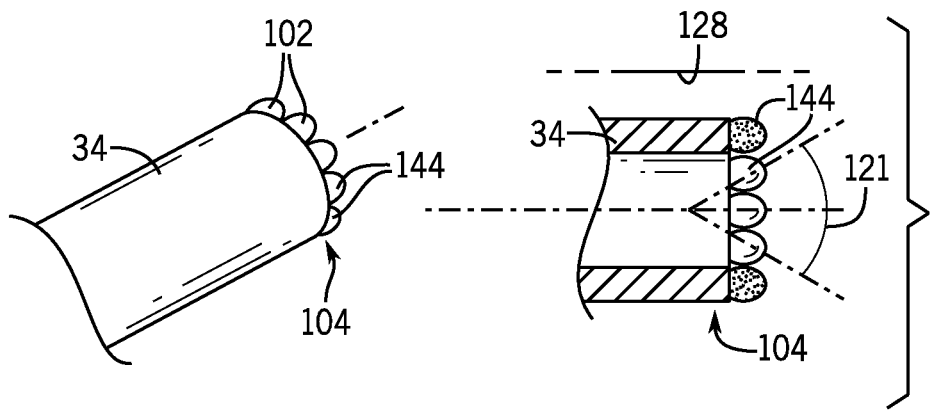
FIG. 14 is a fragmentary perspective view and elevational cross-sectional view of an alternative embodiment providing pressure-sensitive adhesive secured directly to the bore rim of the speculum in the form of small dots or fingers.
Figure 15:
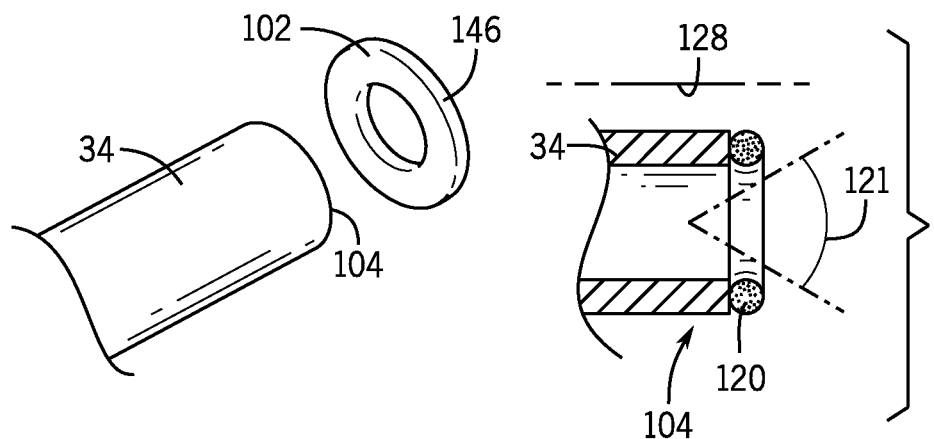
FIG. 15 is a figure similar to that of FIG. 14 showing the dots replaced by a doughnut of pressure-sensitive adhesive.

In these embodiments of FIGS. 14 and 15, actual contact of the rim 104 with the foreign body may be out of focus but may nevertheless be signaled by a high intensity reflected light from the optical fibers 120 (shown in FIG. 9) corralled within the adhesive of the dots 144 or doughnut 146.

Referring momentarily to FIG. 7, it will be appreciated that the funnel-shape 37 of the speculum 10 also serves to stabilize the speculum 10 against the inner walls 128 of the ear canal 130, it's expanding diameter further limiting cross axis translation and angulation of the speculum 10 and thus the propensity of the pressure-sensitive adhesive 102 to have its front surface in contact with oil or wax on the inner walls 128 of the ear canal 130. This is in contrast to a more slender probe which permits greater angulation and the potential for plowing the front surface of the pressure-sensitive adhesive 102 along the earwax in the ear canal 130 thus limiting its effectiveness. Importantly too, the close coupling of the speculum 10 with the otoscope camera 18 (shown in FIG. 9) encourages centering of the pressure-sensitive adhesive 102 within the ear canal 130 driven by the desire to focus on the foreign body 124 and thus away from contamination.

Figure 16:
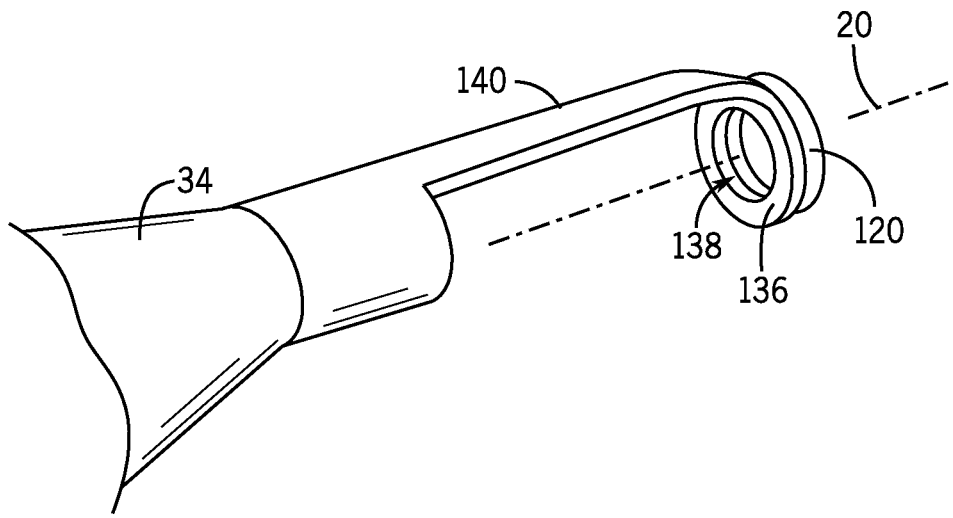
FIG. 16 is a view similar to that of FIGS. 8 and 11 showing a pressure-sensitive adhesive supported on an extension of thermoplastic material of the speculum itself providing benefits of the embodiment of FIG. 11.

Referring now to FIG. 16, it will be appreciated that the probe wire 110 shown in the previous figures may be replaced with a nonmetal and non-ductile material such as a thermoplastic finger 141 being a continuation of the tube 34 of the speculum 10 that may be integrally injection molded to also provide the loop 136 supporting pressure-sensitive adhesive 102 having a central opening 138 on its front face centered along the sight-axis 20. The finger 141 may optionally be provided with a ductile quality by bonding into a ductile material such as a wire.

Figure 17:
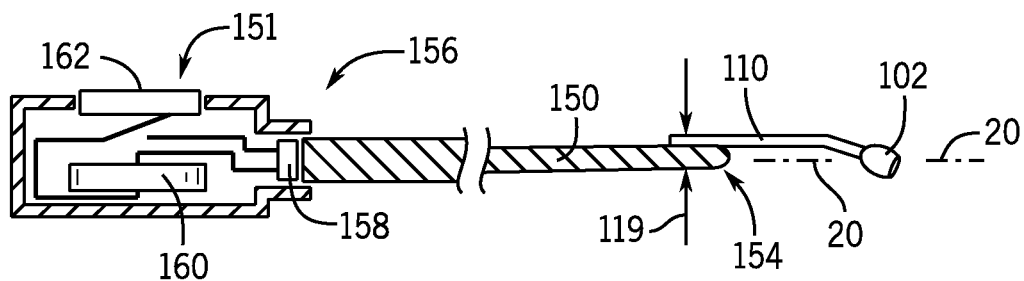
FIG. 17 is a cross-sectional view of a second embodiment of the invention providing an illuminated light pipe serving in the function of the speculum of FIGS. 1-16 and providing a probe wire for spacing the pressure-sensitive adhesive forward from the tip of the light pipe protected within the boundaries of the light pipe periphery.

Referring now to FIG. 17, in a second embodiment, the speculum 34, described above, may be replaced with a light pipe 150, for example, being a solid, transparent thermoplastic material or set of fiber optics extending along axis 20 from a handle unit 152, which may be grasped by the healthcare professional outside of the ear. The light pipe 150 provides a slender probe having a length sufficient to extend from outside the ear into the ear to be proximate to the eardrum. Generally, the diameter of the light pipe 150 will be less than half the average diameter of the ear canal for an average adult to provide sufficient space around the light pipe 150 for viewing inside the ear with the standard otoscope or the like.

In all cases, the light pipe 150 serves to conduct light along its length to a distal tip region 154 that can provide illumination of ear structure and obstructions. A proximal end 156 of the light pipe 150 receives light from a lamp 158, such as a light emitting diode, that may be powered by an internal battery cell 160 within the handle 151. The lamp 158 may be switched into and out of connection with the battery cell 160 by an push button switch 162 accessible from an exposed surface of the handle 151.

As shown in FIG. 17, light discharge from the distal end 154 of the light pipe 150, as conducted from the lamp 158, may pass along the axis 20 to illuminate an obstruction to be removed using the pressure-sensitive adhesive 102. This adhesive 102 may be positioned on a probe wire 110 attached at its proximal end, for example, to a side of the distal end 154 of the light pipe 150 in the manner described above with respect to FIGS. 8 and 11. Alternatively, the pressure-sensitive adhesive 102 may be attached to an integrated extension of the material of the light pipe 150 as described above with respect to FIG. 16, in this case being extension of the material of the light pipe 150 rather than the tube 34. As with the speculum 34 described above, pressure sensitive adhesive 102 may be positioned within the axially extended outer diameter 119 of the light pipe 150 to help protect the pressure-sensitive adhesive from contact with the walls of the ear canal and to allow stabilization of the light pipe 150 against the ear canal with minimal or no contact between the ear canal and the pressure sensitive adhesive 102. The length of the light pipe 150 provides a "reverse" lever helping to stabilize the angular deviation of the light pipe 150 along its axis 20 despite movement of the handle 159 to further prevent such contact.

Figure 18A:
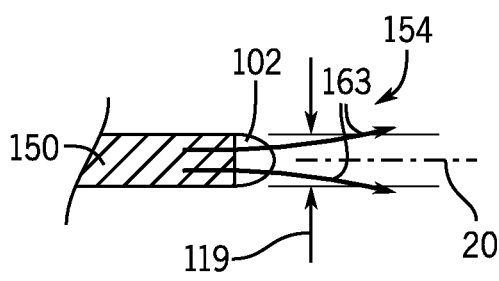
FIGS. 18a and 18b are alternative versions of the embodiment of FIG. 17 employing respectively a transparent pressure-sensitive adhesive through which light may be transmitted and a ring shaped pressure sensitive adhesive similar to that shown in FIGS. 14 and 15.
Figure 18B:
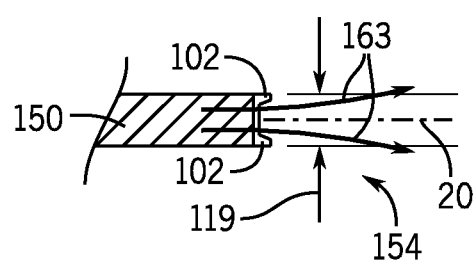

As shown in FIG. 18. alternatively, the pressure sensitive adhesive 102 may be attached directly to the distal end 154 of the light pipe 150 and may be selected to be light transmissive to allow light to be conducted directly from the light pipe 150 through the pressure sensitive adhesive 102 along axially extending rays 163 for illumination of any obstruction. Similarly, as shown in FIG. 19b, a doughnut or other ring-shaped deposition of the pressure sensitive adhesive 102 may be provided on the distal end 154 of the light pipe 105 in the manner disclosed with respect to FIGS. 14 and 15 to allow light passage along rays 162 within the ring-shaped, pressure-sensitive adhesive 102.

The discussion of this preferred embodiment is intended solely for the purpose of providing the public with access to the invention after the expiration of the patent and should not be considered a replacement for the claims or to limit the plain meaning of the claims simply by the recitation of specific preferred features.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. Diameter as used herein is intended to describe an outer periphery of a circle or circumscribing circle in the case of noncircular objects.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

Disclosure of the following US patent publications naming coinventors of the present application are hereby incorporated by reference in their entirety: 20190209001 Otoscope Providing Multi-Directional Illumination; 20180125345 Otoscope Providing Low Obstruction Electronic Display; and 20160374546 Otoscope Providing Multi-Directional Illumination.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A speculum for an otoscope comprising:
a sheath having a proximal sheath end adapted for retention on an otoscope and providing a central bore extending from the proximal sheath end to a bore rim at a distal sheath end along a sight-axis of the otoscope when the sheath is attached to the otoscope; and
a pressure-sensitive adhesive supported through an attachment to the sheath to extend forward from the sheath along the sight-axis to be positioned by a positioning of the sheath into contact with a foreign body within an ear canal to attach to and retract the foreign body from the ear canal.

2. The speculum of claim 1 wherein the sheath provides an outer diameter and the pressure-sensitive adhesive provides a front facing surface positioned within the outer diameter from the sight-axis.

3. The speculum of claim 2 wherein the sheath provides a funnel shape expanding an outer diameter of the sheath toward the proximal sheath end to progressively limit movement of the sheath perpendicular to the sight-axis as the sheath is inserted into the ear canal.

4. The speculum of claim 3 further including an elongate probe having a proximal probe end attached to the distal end of the sheath and sized to extend within the ear canal along the sight-axis to a distal probe end when the proximal sheath end is within the ear canal; and
wherein the pressure-sensitive adhesive attached to a distal probe to extend forward therefrom.

5. The speculum of claim 4 wherein the elongate probe attaches to a wall of the sheath and is displaced from the sight-axis by a radius of a rim of the speculum and extends therefrom displaced away from the sight-axis in a first portion by at least the radius of the rim radius and then curves toward the sight-axis at a second portion further beyond the sheath than the first portion.

6. The speculum of claim 4 wherein the pressure-sensitive adhesive is light transmissive.

7. The speculum of claim 4 wherein the probe provides a loop in a plane perpendicular to the sight-axis for supporting the pressure-sensitive adhesive.

8. The speculum of claim 7 wherein the pressure-sensitive adhesive is distributed around the sight-axis allowing viewing of the foreign body along the sight-axis.

9. The speculum of claim 4 wherein the pressure-sensitive adhesive is displaced from the bore rim along the sight-axis by less than 10 millimeters.

10. The speculum of claim 4 wherein the pressure-sensitive adhesive provides a periphery around the sight-axis enclosing at least five square millimeters.

11. The speculum of claim 4 wherein the pressure-sensitive adhesive has a volume of at least 10 cubic millimeters.

12. The speculum of claim 1 wherein the pressure-sensitive adhesive is distributed around the sight-axis allowing viewing of the foreign body along the sight-axis.

13. The speculum of claim 12 wherein the pressure-sensitive adhesive is attached in contact with the bore rim.

14. The speculum of claim 1 wherein the pressure sensitive adhesive has an adhesive tack strength of greater than 350 measured by Polyken Tack Testing on a 1" square per ASTM D2979-01 using a 5.0 mm probe, 2 mil polyester carrier.

15. A speculum for an otoscope comprising:
a sheath having a proximal sheath end adapted for retention on an otoscope and providing a central bore extending from the proximal sheath end to a bore rim at a distal sheath end along a sight-axis of the otoscope when the sheath is attached to the otoscope; and
a pressure-sensitive adhesive supported by the sheath to extend forward from the sheath along the sight-axis to be guidable by the sheath into contact with a foreign body within an ear canal to attach to and retract the foreign body from the ear canal;
wherein the sheath provides an outer diameter and the pressure-sensitive adhesive provides a front facing surface positioned within the outer diameter from the sight-axis;
wherein the sheath provides a funnel shape expanding an outer diameter of the sheath toward the proximal sheath end to progressively limit movement of the sheath perpendicular to the sight-axis as the sheath is inserted into the ear canal;
further including an elongate probe having a proximal probe end attached to the distal end of the sheath and sized to extend within the ear canal along the sight-axis to a distal probe end when the proximal sheath end is within the ear canal;
wherein the pressure-sensitive adhesive attached to a distal probe to extend forward therefrom; and
wherein the elongate probe is bent to follow a curve at its distal end to present a blunt front-facing surface as it is inserted into the ear canal.

16. A speculum for an otoscope comprising:
a sheath having a proximal sheath end adapted for retention on an otoscope and providing a central bore extending from the proximal sheath end to a bore rim at a distal sheath end along a sight-axis of the otoscope when the sheath is attached to the otoscope; and
a pressure-sensitive adhesive supported by the sheath to extend forward from the sheath along the sight-axis to be guidable by the sheath into contact with a foreign body within an ear canal to attach to and retract the foreign body from the ear canal;
wherein the sheath provides an outer diameter and the pressure-sensitive adhesive provides a front facing surface positioned within the outer diameter from the sight-axis;
wherein the sheath provides a funnel shape expanding an outer diameter of the sheath toward the proximal sheath end to progressively limit movement of the sheath perpendicular to the sight-axis as the sheath is inserted into the ear canal;
further including an elongate probe having a proximal probe end attached to the distal end of the sheath and sized to extend within the ear canal along the sight-axis to a distal probe end when the proximal sheath end is within the ear canal;
wherein the pressure-sensitive adhesive attached to a distal probe to extend forward therefrom; and
wherein the probe provides a ductile material permitting manual adjustment of an angle of extent of the probe from the sheath when the probe is in a relaxed state.

17. An otoscope comprising:
a handgrip for support by a healthcare professional;
a camera stalk extending from the handgrip to a distal end receivable within an ear canal;
a camera positioned at the distal end of the camera stalk to provide a field-of-view therefrom;
a sheath having a proximal sheath end adapted for retention of the otoscope and providing a central bore extending from the proximal sheath end to a bore rim at a distal sheath end along a sight-axis of the otoscope when the sheath is attached to the otoscope; and
a pressure-sensitive adhesive supported by the sheath to extend forward from the sheath along the sight-axis to be guidable by the sheath into contact with a foreign body within an ear canal to attach to and retract the foreign body from the ear canal.

18. The speculum of claim 17 wherein the pressure-sensitive adhesive is sized to occupy no more than half of the field-of-view when centered in the field-of-view.

19. A tool for removing foreign objects from an auditory canal comprising:
a light pipe having an axial extent along an axis and sized to fit within the auditory canal between a proximal and distal end of the light pipe, the light pipe having an outer periphery measured across the axial extent;
a lamp for introducing light into the light pipe at the proximal end for transmission of that light to the distal end; and
a pressure-sensitive adhesive supported by the light pipe to extend forward from the light pipe along the axis to be guidable by the light pipe into contact with a foreign body within an auditory canal to attach to and retract the foreign body from the auditory canal;
wherein at least a portion of the pressure-sensitive adhesive is positioned to be spaced away from the auditory canal when the outer periphery of the light pipe at the proximal end rests against the auditory canal.

20. An attachment for a funnel-shaped speculum of the type having a proximal sheath end adapted for retention on an otoscope and providing a central bore extending from the proximal sheath end to a bore rim at a distal sheath end along a sight-axis of the otoscope when the sheath is attached to the otoscope, the distal sheath end having a reduced diameter from the proximal sheath, the attachment comprising;
a shaft having a proximal end and a distal end;

a pressure sensitive adhesive supported by the distal end of the shaft to extend forward from the proximal end of the shaft; and a collar attached to the proximal end of the shaft and adapted to wrap about the distal sheath end so that the shaft extends along the sight-axis to be guidable by the speculum into contact with a foreign body within an ear canal to attach to and retract the foreign body from the ear canal.

\* \* \* \* \*